(12) United States Patent
Buchanan et al.

(10) Patent No.: US 8,052,624 B2
(45) Date of Patent: Nov. 8, 2011

(54) NEGATIVE PRESSURE, THERMAL ENERGY TRANSFER DEVICE THAT ALSO PROVIDES POSITIVE PRESSURE TO THE PATIENT

(75) Inventors: Richard Buchanan, Hamburg, NY (US); Greg Pepe, Lancaster, NY (US); Gerard E. Kedge, Orchard Park, NY (US); Marcus B. Vail, Williamsville, NY (US)

(73) Assignee: Stryker Corporation, Kalamazoo, MI (US)

( * ) Notice: Subject to any disclaimer, the term of this patent is extended or adjusted under 35 U.S.C. 154(b) by 615 days.

(21) Appl. No.: 12/260,293

(22) Filed: Oct. 29, 2008

(65) Prior Publication Data

US 2010/0106230 A1  Apr. 29, 2010

(51) Int. Cl.
*A61H 7/00* (2006.01)
*A61F 7/00* (2006.01)
(52) U.S. Cl. ............................ 601/11; 607/104; 607/111
(58) Field of Classification Search ................ 601/6, 11; 607/96, 104, 107, 108, 111, 112
See application file for complete search history.

(56) References Cited

U.S. PATENT DOCUMENTS

| | | | |
|---|---|---|---|
| 1,199,914 A | 10/1916 | Mossor | |
| 1,202,605 A | 10/1916 | Storm, Jr. | |
| 1,549,510 A | 8/1925 | Schnitzler | |
| 2,113,253 A | 4/1938 | Gray | |
| 2,832,336 A | 4/1958 | Davis et al. | |
| 3,156,237 A | 11/1964 | Edmark, Jr. | |
| 3,186,404 A | 6/1965 | Gardner | |
| 3,450,450 A | 6/1969 | Hopkins et al. | |
| 3,516,411 A | 6/1970 | Adler | |
| 3,785,374 A | 1/1974 | Lipson | |
| 3,859,989 A | 1/1975 | Spielberg | |
| 4,139,004 A | 2/1979 | Gonzalez, Jr. | |
| 4,870,251 A | 9/1989 | Anemaet | |
| 4,966,135 A | 10/1990 | Renfrew | |
| 5,000,164 A | 3/1991 | Cooper | |
| 5,074,285 A | 12/1991 | Wright | |
| 5,554,103 A | 9/1996 | Zheng et al. | |
| 5,683,438 A | 11/1997 | Grahn | |
| 5,688,225 A | 11/1997 | Walker | |
| 5,755,275 A | 5/1998 | Rose et al. | |
| 5,893,368 A | 4/1999 | Sugerman | |
| 5,938,626 A | 8/1999 | Sugerman | |
| 6,149,674 A | 11/2000 | Borders | |
| 6,245,094 B1 | 6/2001 | Pompei | |
| 6,517,510 B1 | 2/2003 | Stewart et al. | |
| 6,530,941 B1 | 3/2003 | Müller et al. | |
| 6,565,593 B2 | 5/2003 | Diana | |
| 6,602,277 B2 | 8/2003 | Grahn et al. | |
| 6,656,208 B2 | 12/2003 | Grahn et al. | |
| 6,673,099 B2 | 1/2004 | Grahn et al. | |

(Continued)

*Primary Examiner* — Nicholas Lucchesi
*Assistant Examiner* — Nathan R Price
(74) *Attorney, Agent, or Firm* — Warner Norcross & Judd LLP (57) ABSTRACT

A negative pressure, thermal energy device has an enclosure that receives a patient's body part. The body part is positioned in the enclosure and contacts a thermal energy contacting surface. The thermal energy contacting surface transfers its thermal energy to the body part. While in the enclosure, the body part is also exposed to a negative pressure to cause vasodilation. The combination of the vasodilation and the thermal energy transfer alter the patient's body core temperature. To ensure the body part remains in contact with the thermal contacting surface, the enclosure has a portion thereof that moves when negative pressure is in the enclosure. When the negative pressure is applied, the deforming enclosure material is pulled toward the body part to provide a positive pressure on the body part that ensures the body part effectively contacts the thermal energy contacting surface.

20 Claims, 5 Drawing Sheets

U.S. PATENT DOCUMENTS

| | | |
|---|---|---|
| 6,916,289 B2 | 7/2005 | Schnall |
| 6,966,922 B2 | 11/2005 | Grahn et al. |
| 6,974,442 B2 | 12/2005 | Grahn et al. |
| 7,122,047 B2 | 10/2006 | Grahn et al. |
| 7,182,776 B2 | 2/2007 | Grahn et al. |
| 7,540,848 B2 | 6/2009 | Hannigan et al. |
| 7,591,795 B2 | 9/2009 | Whalen et al. |
| 7,618,382 B2 | 11/2009 | Vogel et al. |
| 2002/0019657 A1 | 2/2002 | Elkins |
| 2003/0032904 A1 | 2/2003 | Egger |
| 2003/0040783 A1 | 2/2003 | Salmon |
| 2004/0010212 A1 | 1/2004 | Kuiper et al. |
| 2004/0039432 A1 | 2/2004 | Warriner |
| 2004/0064169 A1 | 4/2004 | Briscoe et al. |
| 2004/0082886 A1 | 4/2004 | Timpson |
| 2005/0203452 A1 | 9/2005 | Weston et al. |
| 2005/0251117 A1 | 11/2005 | Anderson et al. |
| 2005/0261615 A1 | 11/2005 | Weston |
| 2006/0100556 A1 | 5/2006 | Hargens et al. |
| 2006/0111766 A1 | 5/2006 | Grahn et al. |
| 2006/0122670 A1 | 6/2006 | Grahn et al. |
| 2006/0235346 A1 | 10/2006 | Prescott |
| 2006/0287621 A1 | 12/2006 | Atkinson et al. |
| 2007/0055188 A1 | 3/2007 | Avni et al. |
| 2007/0060987 A1 | 3/2007 | Grahn et al. |
| 2007/0093730 A1 | 4/2007 | Chan et al. |
| 2007/0112400 A1 | 5/2007 | Hamilton |
| 2007/0123962 A1 | 5/2007 | Grahn et al. |
| 2007/0167884 A1 | 7/2007 | Mangrum et al. |
| 2007/0198072 A1 | 8/2007 | Montain et al. |
| 2008/0000484 A1 | 1/2008 | Kaiser |
| 2008/0021531 A1 | 1/2008 | Kane et al. |
| 2008/0064992 A1 | 3/2008 | Stewart et al. |
| 2008/0077202 A1 | 3/2008 | Levinson |
| 2008/0077205 A1 | 3/2008 | Cazzini |
| 2008/0132816 A1 | 6/2008 | Kane |
| 2008/0132976 A1 | 6/2008 | Kane |
| 2008/0228248 A1 | 9/2008 | Guyuron et al. |
| 2008/0234788 A1 | 9/2008 | Wasowski |
| 2008/0249593 A1 | 10/2008 | Cazzini et al. |
| 2009/0005840 A1 | 1/2009 | Harty |
| 2009/0014004 A1 | 1/2009 | Whalen et al. |
| 2009/0048547 A1 | 2/2009 | Chen |
| 2009/0120433 A1 | 5/2009 | Loori et al. |
| 2009/0259169 A1 | 10/2009 | Loori et al. |
| 2009/0312675 A1 | 12/2009 | Sampson et al. |
| 2010/0010408 A1 | 1/2010 | Linares |
| 2010/0095641 A1 | 4/2010 | Ruetenik |
| 2010/0152821 A1 | 6/2010 | Rein et al. |

NEGATIVE PRESSURE, THERMAL ENERGY TRANSFER DEVICE THAT ALSO PROVIDES POSITIVE PRESSURE TO THE PATIENT

FIELD OF THE INVENTION

The present invention relates to negative pressure, thermal energy transfer units for controlling, maintaining and/or adjusting the body core temperature of a mammal, in particular a human.

BACKGROUND OF THE INVENTION

Stanford University is the assignee of U.S. Pat. Nos. 5,683,438; 6,602,277; 6,673,099; 6,656,208; 6,966,922; 7,122,047; and 6,974,442. These patents disclose a negative pressure, thermal energy device that can be applied to a patient. The negative pressure device has the following elements: (1) a hard, non-shape altering enclosure having an opening to receive a portion of a patient's body that contains a venous plexus area, (2) a vacuum system that creates a negative pressure in the enclosure, (3) a seal positioned at the enclosure's opening to maintain the negative pressure in the enclosure, and (4) a thermal energy system having a thermal energy contacting element wherein the venous plexus area is exposed to the thermal energy from the thermal energy contacting element.

Enclosure

The enclosure surrounds a portion of a patient's body. In a preferred embodiment, the portion of the patient's body has a venous plexus area. The venous plexus area is a vascular network formed by numerous anastomoses between arteries and veins. A venous plexus area is, along with other locations, normally located at the patient's foot area and/or hand area.

The enclosure can be shaped like a glove, a mitten, a boot, a clam-shell, or equivalents thereof so long as there is an opening that receives the patient's body part. In many embodiments, the enclosure is a polymeric material that can withstand the formation of predetermined negative pressure values within its interior that receives the patient's body part.

Seal

The seal is mounted at the enclosure's opening that receives the patient's body part having a venous plexus area. The seal establishes (1) a vacuum-tight fit between the body portion and the enclosure or (2) a soft seal fit between the body portion and the enclosure.

The term "vacuum-tight", as interpreted by Dr. Grahn in some of the above-identified Stanford patents and he is one of the inventors of all of the Stanford patents, means a hard seal. In U.S. Pat. No. 7,182,776; Dr. Grahn wrote, "A "hard" seal is characterized as one designed to altogether avoid air leakage past the boundary it provides. In theory, a "hard" seal will allow a single evacuation of the negative pressure chamber for use in the methods. In practice, however, a "hard" seal can produce a tourniquet effect. Also, any inability to maintain a complete seal will be problematic in a system requiring as much."

A "soft" seal as described herein is characterized as providing an approximate or imperfect seal at a user/seal interface. Such a seal may be more compliant in its interface with a user. Indeed, in response to user movement, such a seal may leak or pass some air at the user/seal interface. In a negative-pressure system designed for use with a soft seal, a regulator or another feedback mechanism/routine will cause a vacuum pump, generator, fan or any such other mechanism capable of drawing a vacuum to respond and evacuate such air as necessary to stabilize the pressure within the chamber, returning it to the desired level. Active control of vacuum pressure in real-time or at predetermined intervals in conjunction with a "soft" seal provides a significant advantage over a "hard" seal system that relies on simply pulling a vacuum with the hopes of maintaining the same.

Some of the Stanford patents disclose the seal is long to "Provide greater seal surface contact with a user." Greater seal surface contact to the patient increases tissue interface pressure. Increased tissue interface pressure is undesirable.

Vacuum System

The vacuum system connects to the enclosure for generating and, in some embodiments, maintaining a predetermined negative pressure inside the enclosure to cause vasodilation in the body portion surrounded in the enclosure. Negative pressure conditions are a pressure lower than ambient pressure under the particular conditions in which the method is performed. The magnitude of the decrease in pressure from the ambient pressure under the negative pressure conditions is generally at least about 20 mmHg, usually at least about 30 mmHg and more usually at least about 35 mmHg, where the magnitude of the decrease may be as great as 85 mmHg or greater, but typically does not exceed about 60 mmHg and usually does not exceed about 50 mmHg. The negative pressure applied to a portion of the body in the enclosure (a) decreases the temperature when vasoconstriction occurs and/or (b) increases the vasodilation in the body portion that is in the enclosure.

The negative pressure inducing element may be actuated in a number of different ways, including through motor driven aspiration, through a system of valves and pumps which are moved through movement of the mammal in a manner sufficient to create negative pressure in the sealed environment, etc.

Thermal Energy Contacting Element

The thermal energy contacting element transfers thermal energy to, or extracts thermal energy from the body portion in the vacuum enclosure. Whether the thermal energy transfers to or extracts from the body portion depends on the relative temperatures of the thermal energy contacting element and the body portion. The vasodilation in the body portion enhances the exchange of thermal energy between a patient's body core, surface of the body portion, and the thermal energy contacting element.

The thermal energy contacting element has been previously disclosed as (a) a conventional thermal warming plate or blanket, or a conventional thermal cooling plate or blanket, (b) a warm or cool water immersion element, (c) a warming or cooling gas element, and (d) a curved metal plate or a metal tube positioned in the interior of the enclosure.

The three latter embodiments deal with a fluid. In the conduit embodiments, the fluid (i) circulates within it and (ii) does not contact the body portion in the desired area—the venous plexus area. The fluid can be provided by a hypo/hyper/normothermia fluid temperature control device. An example of such a device, and not limited to, is Gaymar's Medi-Therm II hypo/hyper/normothermia fluid temperature control device. That device is disclosed and incorporated by reference in commonly assigned U.S. Pat. No. 6,517,510.

There are problems with the thermal energy contacting surfaces, a patient could elect (a) not to grip the thermal energy contacting element, (b) to re-position the body part, so the body part is not affected by the thermal energy contacting element or (c) to loosen (for example blanket embodiments) the thermal energy contacting element so it does not effectively contact the body part. The patient's election may be unintentional especially if the patient is sedated or under general anesthesia. It is therefore at least one object of the present invention to solve this potential contact problem by making the device invariant to a patient's desire to "grip" or contact the thermal energy contacting element.

Of these thermal energy contacting element embodiments, the metal plate and tube are considered by many to be an effective thermal energy contacting elements because (a) those components are easy to manufacture, (b) the thermal energy transfer efficiency to the patient is relatively acceptable and (c) using the product in actual use is easy.

SUMMARY OF THE INVENTION

A negative pressure, thermal energy device has an enclosure that receives a patient's hand or foot. The hand or foot is positioned in the enclosure and contacts a thermal energy contacting surface. The thermal energy contacting surface transfers its thermal energy to the patient. While in the enclosure, the hand and foot is also exposed to a negative pressure to cause vasodilation. The combination of the vasodilation and the thermal energy transfer, alters the patient's body core temperature. When the enclosure is just a non-shape altering material, the above-description is clearly disclosed in the prior art. A problem with the prior art is that if the patient moves its hand or foot from the thermal contacting surface, the patient does not receive the desired transfer of thermal energy. To ensure the patient's hand or foot remains in contact with the thermal contacting surface, the enclosure has portion thereof that is a shape altering material. When the negative pressure is applied to the shape altering material, the shape altering material is pulled toward the hand or foot to (a) provide a positive pressure on the hand or foot and (b) ensure the hand or foot effectively contacts the thermal energy contacting surface.

DETAILED DESCRIPTION OF THE INVENTION

Figure 1:
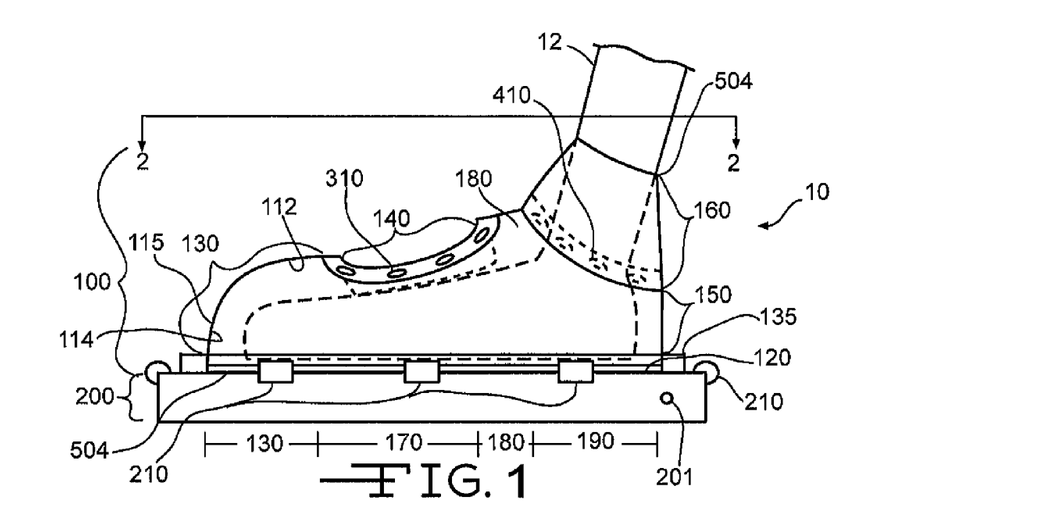
FIG. 1 illustrates a side view of the present invention.
Figure 2:
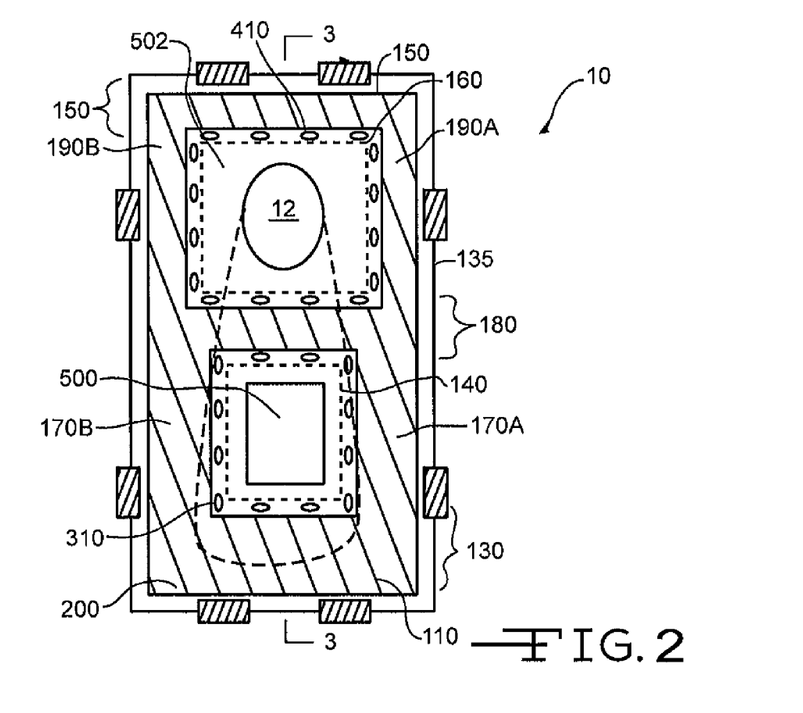
FIG. 2 is a top view of FIG. 1 taken along the lines 2-2.
Figure 3:
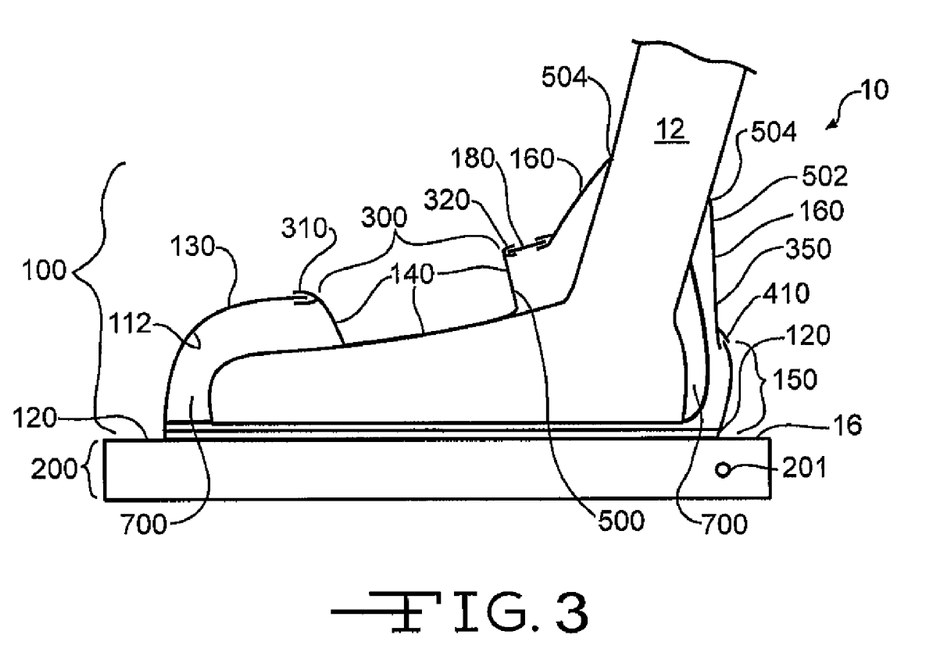
FIG. 3 is a cross-sectional view of FIG. 2 taken along the lines 3-3.

Turning to FIGS. 1, 2 and 3, the present invention is directed to a thermal-energy, negative pressure device 10. For ease of reference, we have incorporated a patient's foot, not claimed, in the thermal-energy, negative pressure device 10 illustrated in FIGS. 1, 2 and 3. Obviously a patient's hand could have been illustrated as well. This thermal-energy, negative pressure device 10 can be divided into sections.

The sections include and are not limited to a contact section 100 and an operation section 200. As illustrated at FIG. 1, the contact section 100 has components that enclose the patient's foot. The operation section 200 has the components that (a) create the negative-pressure in the contact section 100, (b) generate or provide the desired thermal energy that the patient's foot experiences in the contact section 100, and (c) in one embodiment, contact the patient's foot.

Contact Section

The contact section 100 is further divided into a hard shell (a.k.a., a non-shape altering, air impermeable enclosure) 110, a sole material (a.k.a., an air permeable, thermal transfer pad) 120, a pressure contact area 140, and a sealing area 160. Collectively and in one embodiment, the hard shell 110, the sole material 120, the pressure contact area 140, and the sealing area 160 have an interior surface 114 and an exterior surface 115. The interior surface 114 defines a cavity 112. The cavity 112 receives the patient's foot.

Figures 4, 5:
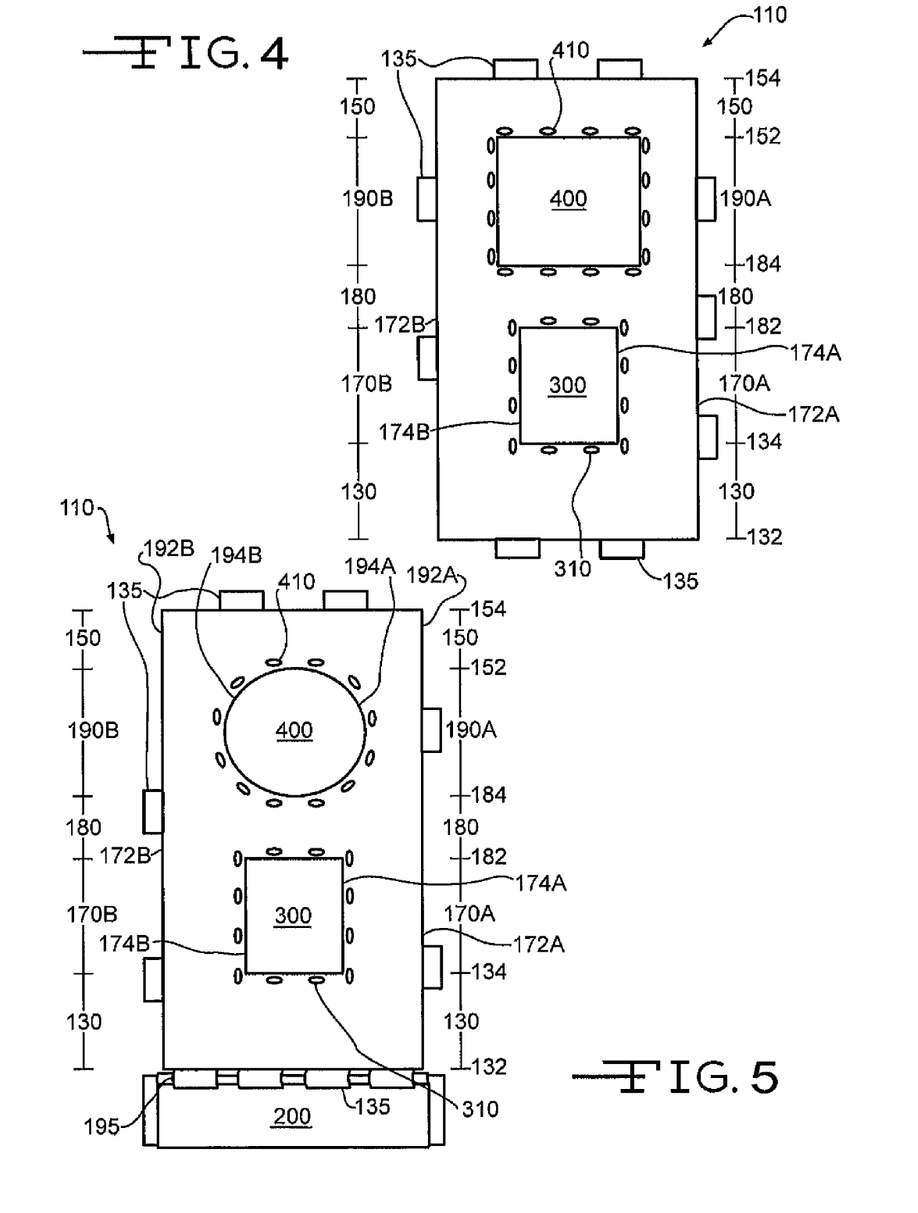
FIG. 4 is a top view of FIG. 1 without the body part and the shape altering, air impermeable materials.
FIG. 5 is an alternative embodiment of FIG. 4 wherein a hinge connects a portion of the contact section to the operation section.

The hard shell area 110, as illustrated in FIGS. 2, 4, and 5, includes a toe area 130, a ledge 135, a first middle area 170A, a second middle area 170B, a transition support area 180, a first ankle area 190A, a second ankle area 190B, a heel area 150, a positive pressure opening 300, an appendage opening 400, and a negative pressure opening 700. See FIG. 3. The ledge 135 and the negative pressure opening 700 define a base area 116. From the base area 116, the hard shell area 110 extends upwards and sometimes toward the middle of the hard shell area 110.

The ledge 135 (a) circumvents the base area 116 of the hard shell area 110 as illustrated at FIG. 2, (b) is interspaced about the base area 116 of the hard shell area 110 as illustrated at FIG. 4, or (c) interspaced about portions of the base of the hard shell area 110 and having one base edge releasably interconnected, for example and not limited to a hinge embodiment 195, to the operation section 200 as illustrated at FIG. 5. The ledge 135 provides a surface for the sole material 120 to be removably positioned at the base area 116 of the hard shell 110 and between the hard shell 110 and the operation section 200. The ledge 135 also provides a surface for clips 210 (see FIG. 1) or equivalents thereof to removably secure the operation section 200 to the hard shell 110. The clips 210 could be an integral part of the operation section 200, the ledge 135, or removably connected to the operation section 200 and the ledge 135.

The hard shell area 110 is made of durable, hard thermoplastic material that is preferably air impermeable and non-shape altering. Non-shape altering means the hard shell 110 does not alter its shape when it is subjected to a negative pressure used in the normal operation of this device 10. An example of that durable, hard thermoplastic material is a polycarbonate material, a polypropylene material, a polyethylene material or combinations thereof. A specific example includes and is not limited to Bayer Material Science AG's Makrolon® 2658 polycarbonate. Whatever durable, hard thermoplastic material is used, the material should be injection moldable to form the ledge 135, the toe area 130, the first and second middle areas 170a,b, the transition support area 180, the first and second ankle areas 190a,b, and the heel area 150. In addition, the durable, hard thermoplastic material should not be an irritant to the patient's skin.

As illustrated in FIGS. 4 and 5, the toe area 130 has a distal end 132 and a proximal end 134; the transition support area 180 has a distal end 182 and a proximal end 184. The heel area 150 has a base end 152 and a top end 154. The base end 152 and the top end 154 can be in relation to the ledge perpendicular to each other as illustrated in FIG. 1, or angled in relation to each other.

The first middle area 170a has a base end 172a at the hard shell's base 116 and a top end 174a; and the second middle area 170b has a base end 172b at the hard shell's base 116 and a top end 174b. The top ends 174a,b do not meet each other, are spaced away from the respective base ends 172a,b; and are equal to or, preferably, closer to the distance between the base ends 172a,b.

The first ankle area 190a has a base end 192a at the hard shell's base 116 and a top end 194a; and the second ankle area 190b has a base end 192b at the hard shell's base 116 and a top end 194b. The top ends 194a,b do not meet each other, are spaced away from the respective base ends 192a,b; and are equal to or, preferably, closer to than the distance between the base ends 192a,b.

The positive pressure opening 300 is defined in the hard shell 110 by a portion of the toe area's proximal end 134, a portion of the transition support area's distal end 184, and the top ends 174a,b of the respective first and second middle areas 170a,b. The positive pressure opening 300 is a first predetermined distance from the base 116. The first predetermined distance is sufficient to allow the patient's foot in the cavity which means the top of the patient's foot, for the average patient, should not contact the interior surface 114 that defines the positive pressure opening 300.

A first set of secure openings 310 in the hard shell 110 are spaced a pre-set distance from the positive pressure opening 300. The first set of secure openings 310 also surrounds the positive pressure opening 300. The first set of secure openings 310 are designed to secure a first air impermeable, shape altering thermoplastic material 500 (a) to the hard shell 110 and (b) over the positive pressure opening to form the pressure contact area 140.

Figure 6A:
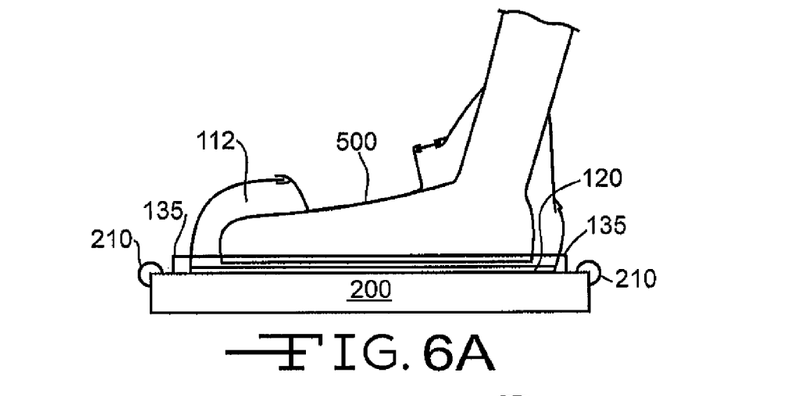
FIG. 6A is a cross-section of FIG. 1 with positive pressure being applied in the negative pressured cavity.
Figure 6B:
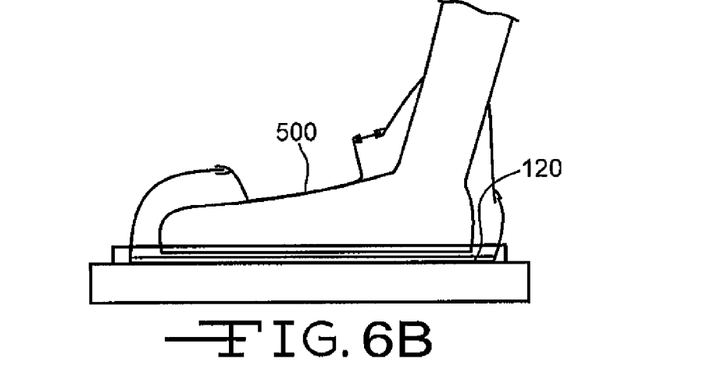
FIG. 6B is a cross-section of FIG. 6A with no negative pressured cavity.

The first air impermeable, shape altering thermoplastic material 500 is overmolded to the hard shell 110 and by default over and/or at the positive pressure opening 300. The term "shape altering" means the thermoplastic material will (a) alter its shape when it is subjected to a negative pressure used in the normal operation of this device 10, and (b) essentially revert to its original shape or close to its original shape when it is not subjected to negative pressure. For example, when negative pressure is present in the cavity 112, the first air impermeable, shape altering material 500 is drawn or pulled to the patient's foot. The negative pressured embodiment has the material 500 apply a positive pressure force against the patient's foot to ensure the patient's foot contacts the sole material 120 as illustrated in FIG. 6A. FIG 6B illustrates a non-negative pressure embodiment wherein the material 500 reverts to its original or close to original position that does not, should not, exert a positive pressure force against the patient's foot.

When the first air impermeable, shape altering thermoplastic material 500 is overmolded to the hard shell 110, a portion of the first air impermeable, shape altering thermoplastic material 500 is positioned on (a) the exterior surface 115 possibly between the first set of secure openings 310 and the positive pressure opening 300 and possibly just beyond the first set of secure openings 310 away from the positive pressure opening 300 (see FIGS. 1, 2, 6A and 6B) and (b) the interior surface 114 possibly between the first set of secure openings 310 and the positive pressure opening 300 and possibly just beyond the first set of secure openings 310 away from the positive pressure opening 300 of the hard shell 110 (see FIGS. 6A and 6B). That way the first air impermeable, shape altering thermoplastic material 500 is securely attached to the hard shell 110.

The appendage opening 400 is also defined in the hard shell 110 by a portion of the heel area top end 154, a portion of the transition support area's proximal end 184, and the top ends 194a,b of the respective first and second ankle areas 190a,b. The appendage opening 400 is sufficient to allow the patient's foot in the cavity 112 which means the top of the patient's foot, for the average patient, should not contact the interior surface 114 of the hard shell 110 that defines the appendage opening 300.

A second set of secure openings 410 in the hard shell 110 are spaced a pre-set distance from the appendage opening 400. The second set of secure openings 410 also surrounds the appendage opening 400. The second set of secure openings 410 are designed to secure a second air impermeable, shape altering thermoplastic material 502 (a) to the hard shell 110 and (b) over the appendage opening 400 with an aperture 504 to receive the patient's foot and part of the patient's leg to form the sealing area 160.

The second air impermeable, shape altering thermoplastic material 502 is overmolded to the hard shell 110 and by default over the appendage opening 400. When the second air impermeable, shape altering thermoplastic material 502 is overmolded to the hard shell 110, a portion of the second air impermeable, shape altering thermoplastic material 502 is positioned on (a) the exterior surface 115 possibly between the second set of secure openings 410 and the appendage opening 400 and possibly just beyond the second set of secure openings 410 away from the appendage opening 400 and (b) the interior surface 114 possibly between the second set of secure openings 410 and the appendage opening 400 and possibly just beyond the second set of secure openings 410 away from the appendage opening 400 of the hard shell 110. That way the second air impermeable, shape altering thermoplastic material 502 is securely attached to the hard shell 110.

The first and second air impermeable, shape altering thermoplastic materials 500, 502 can be the same material or different materials. In many cases the two thermoplastic materials 500, 502 are the same. In any case, the first and second air impermeable, shape altering thermoplastic materials 500, 502 are non-rigid, pliable polymeric material that can move in response to negative pressure. A preferred, but not limited to, first and second air impermeable, pliable thermoplastic material 500, 502, is GLS corporation's Versaflex® CL2000X TPE alloy or variations thereof. A common characteristic of the first and second air impermeable, shape altering thermoplastic materials 500, 502 is that each material creates a soft touch to the patient's body part when the material contacts the body part. Another common characteristic is that the materials 500, 502 move toward the patient's foot in response to a negative pressure being applied within the cavity 112. That movement is the basis for the first and second thermoplastic materials 500, 502 being defined as air impermeable and shape altering. That movement in the second air impermeable, shape altering thermoplastic material 502 secures the material around the aperture 504 to the patient to create an air impermeable seal around the patient's leg. That movement in the first air impermeable, shape altering thermoplastic material 500 applies a positive pressure upon the patient's foot so it forces the patient's foot toward the sole material 120 to ensure the patient's foot remains in contact with the sole material 120 to obtain the maximize the transfer of thermal energy to the patient.

Sole Material

The hard shell 110, the first air impermeable, pliable thermoplastic material 500, the second air impermeable, pliable thermoplastic material 502, and the operation section 200 (to be discussed later) are permanent components of the device 10. In contrast, the sole material 120 is a replaceable material positioned over and/or at the negative pressure opening 700. In particular the sole material 120 can be replaced after every use by a patient or between patients. For hygiene purposes, the applicant recommends replacing the sole material 120 after each use.

The sole material 120 is a barrier material that could provide bacteria penetration resistance, tear strength, and puncture resistance. The barrier material does not inhibit the transfer of thermal energy from the operation system 200 or inhibit the formation and maintaining of a negative pressure environment in the cavity 112 through the operation system 200. An example of that material, and not limited to that material, is DuPont Corporation's Tyvek® material.

Figure 7:
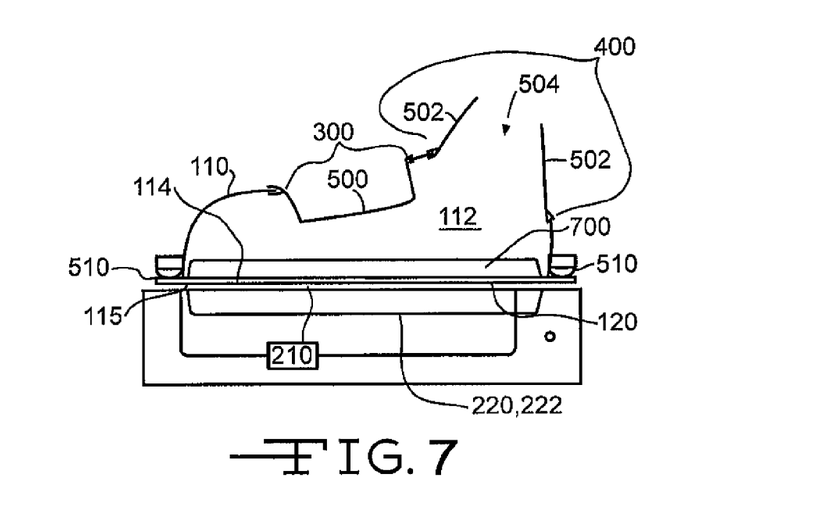
FIG. 7 is a slightly exploded view of FIG. 6A without a foot therein and illustrating a cross-sectional view of the operating section.

The sole material 120 can have a perimeter that corresponds with the hard shell's base area 116 perimeter. The sole material's perimeter can also have an adhesive that contacts to the base area 116, which can also have a third air impermeable, shape altering thermoplastic material 510 (same material as the first and/or second air impermeable, pliable thermoplastic material 500, 502) overmolded on the base area 116. Once the sole material 120 (a) is removably attached to the base area 116 or the third air impermeable, shape altering thermoplastic material 504 and (b) covers negative pressure opening 700, the sole material 120 forms the contact section 100 with the interior surfaces 114 of the hard shell 110, the first air impermeable, shape altering thermoplastic material 500, the second air impermeable, shape altering thermoplastic material 502; and the interior surface 114 of the sole material 120 defines the cavity 112 with the interior surfaces 114 of the hard shell 110, the first air impermeable, shape altering thermoplastic material 500, the second air impermeable, shape altering thermoplastic material 502. (See FIG. 7)

The exterior surface 115 of the sole material 120 contacts the operation system 200.

Operation System

The operation system 200 is a container having a perimeter that corresponds to the perimeter of the hard shell's base area 112. The operation system 200 has a top surface, which contacts the sole material's exterior surface 120, 115 or alternatively is a surface that helps defines the cavity 112 if the sole material 120 is not used. The operation system 200 also has sufficient space, preferably compact, to contain a conventional vacuum source 210 and a conventional thermal energy source 220.

Thermal Energy Contacting Element

Figure 8:
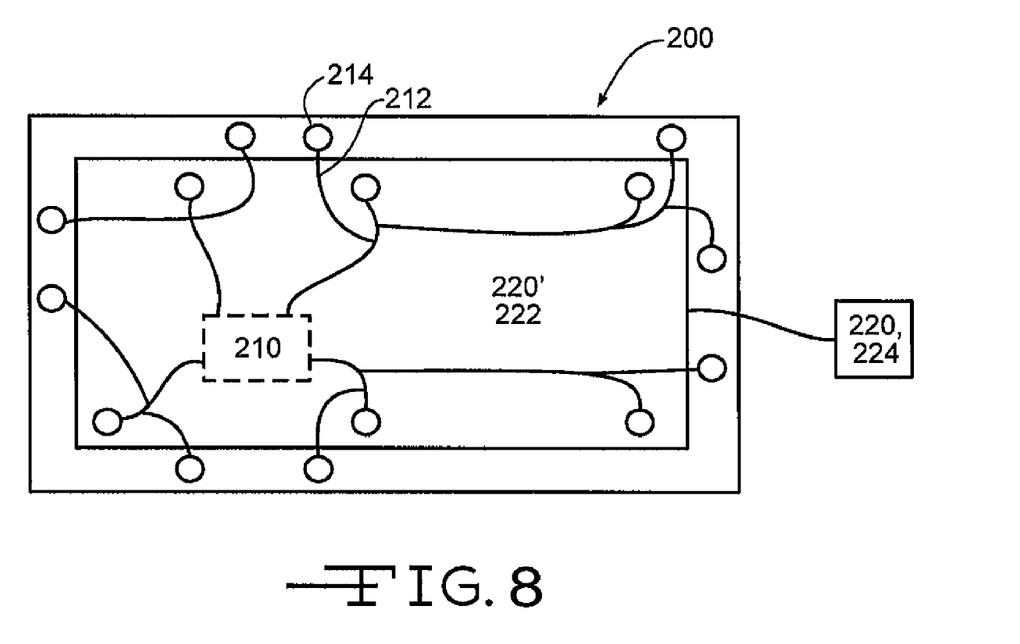
FIG. 8 is a top view of the operating section of FIG. 7.

The thermal energy source 220 (see FIG. 8) has a thermal energy contacting element 222 that transfers thermal energy to, or extracts thermal energy from the body 5 portion in the negative pressured enclosure and a source 224 that provides the energy to run the contacting element 222 or provide fluid at a desired temperature to the element 222. Whether the thermal energy transfers to or extracts from the foot depends on the relative temperatures of the thermal energy contacting element and the foot. The vasodilation in the foot enhances the exchange of thermal energy between a patient's body core, surface of the foot, and the thermal energy contacting element.

The thermal energy contacting element has been previously disclosed as (a) a conventional thermal warming plate or blanket, or a conventional thermal cooling plate or blanket, (b) a warm or cool water immersion element, (c) a warming or cooling gas element, and (d) a curved metal plate or a metal tube positioned in the interior of the enclosure.

The three latter embodiments can have a fluid (i) circulate within it and (ii) not contact the body portion in the desired area—the venous plexus area. The fluid can be provided by a hypo/hyper/normothermia fluid temperature control device. An example of such a device, and not limited to, is Gaymar's Medi-Therm II hypo/hyper/normothermia fluid temperature control device. That device is disclosed and incorporated by reference in commonly assigned U.S. Pat. No. 6,517,510.

Obviously, the electrical energy is supplied through an electrical conduit interconnected to an electrical source, and the hypo/hyper/normothermia fluid temperature control device is interconnected to the operation system 200 through a fluid conduit.

Vacuum System

The vacuum system 210 has conduits that draw the air from the cavity 112 through vacuum apertures 214 and the pad 120, if used, to create the desired negative pressure in the cavity 112. The system 210 connects to the enclosure for generating and, in some embodiments, maintaining a predetermined negative pressure inside the enclosure to cause vasodilation in the body portion surrounded in the enclosure. Negative pressure conditions are a pressure lower than ambient pressure under the particular conditions in which the method is performed. The magnitude of the decrease in pressure from the ambient pressure under the negative pressure conditions is generally at least about 20 mm Hg, usually at least about 30 mm Hg and more usually at least about 35 mm Hg, where the magnitude of the decrease may be as great as 85 mm Hg or greater, but typically does not exceed about 60 mm Hg and usually does not exceed about 50 mm Hg. The negative pressure applied to a portion of the body in the enclosure (a) decreases the temperature when vasoconstriction occurs and/or (b) increases the vasodilation in the body portion that is in the enclosure.

The negative pressure inducing element may be actuated in a number of different ways, including through motor driven aspiration, through a system of valves and pumps which are moved through movement of the mammal in a manner sufficient to create negative pressure in the sealed environment, etc.

In this invention, it is preferred the vacuum system 210 modulates its negative pressure in the cavity 112 from −60 mm Hg to −10 mm Hg, and preferably −40 mm Hg to −25 mm Hg. That modulation ensures the patient is not under a constant negative pressure. Constant negative pressure is undesired because the patient's body can become acclimated to the pressure and not cause vasodilation. Accordingly, it is desired that the negative pressure is modulated to retain and maintain the desired vasodilation effect.

The operation system 200 also has a leak aperture 201 that allows ambient air at a controlled rate to enter the cavity 112. That leaked ambient air decreases the chances of the first and/or second shape altering, air impermeable material 500, 502 from essentially becoming a tourniquet to the patient.

It is appreciated that various modifications to the inventive concepts described herein may be apparent to those of ordinary skill in the art without departing from the spirit and scope of the present invention as defined by the appended claims. Furthermore, while the present invention has been described with respect to a negative pressure, thermal energy device applied to a person's foot that should not be viewed as limiting its scope. Those skilled in the art after having read the present description will readily understand that the various enclosure structures are equally applicable for use with a patient's hand.

We claim:

1. A negative pressure, thermal energy device comprising:
    a non-shape altering, air impermeable enclosure having an appendage opening, a positive pressure opening, and a negative pressure opening;
    a first shape altering, air impermeable material positioned at the appendage opening, securely attached to the non-shape altering enclosure, and having an aperture to receive a portion of a patient's appendage;

a second shape altering, air impermeable material positioned at the positive pressure opening and securely attached to the non-shape altering, air impermeable enclosure;
an air permeable, thermal transfer pad (a) removably attached to the non-shape altering, air impermeable enclosure, (b) positioned at the negative pressure opening, and (c) having a top surface and a bottom surface;
(a) the non-shape altering, air impermeable enclosure, (b) the first shape altering, air impermeable material, (c) the second shape altering, air impermeable material, and (d) the air permeable, thermal transfer pad define a cavity;
an operating container
  (a) that releasably attaches to the non-shape altering enclosure,
  (b) has a thermal energy contacting surface that
    (i) contacts at least a portion of the air permeable, thermal transfer pad's bottom surface,
    (ii) transfers thermal energy through the air permeable, thermal transfer pad to the patient's body surface that contacts the air permeable, thermal transfer pad and
    (iii) interconnects to or is a component of a thermal energy generating device; and
  (c) has a vacuum source that generates a negative pressure in the cavity, the negative pressure in the cavity is sufficient to cause
    (i) the patient's veins in the cavity to vasodilate, and
    (ii) the second shape altering, air impermeable material to be pulled toward the patient to provide a positive pressure on the patient that ensures the patient's body part contacts the air permeable, thermal transfer pad.

2. The device of claim 1 wherein the negative pressure modulates.

3. The device of claim 2 wherein the negative pressure modulates between −25 and −40 mmHg.

4. The device of claim 1 wherein the operating container has a leak aperture that allows ambient air to enter the cavity.

5. The device of claim 4 wherein the leak aperture diminishes the chances that the first shape altering, air impermeable material will create a tourniquet effect on the patient.

6. The device of claim 1 wherein the thermal energy contacting surface defines a portion of a conduit, the conduit interconnects to the thermal energy generating device, the thermal energy generating device is a hyper/hypo/normothermia fluid temperature control device, the hyper/hypo/normothermia fluid temperature control device controls the temperature of the fluid, and the fluid at the predetermined temperature circulates in the conduit.

7. The device of claim 1 wherein the thermal energy contacting surface and the thermal energy generating device is a thermal heating plate or blanket.

8. The device of claim 1 wherein the thermal energy contacting surface and the thermal energy generating device is a thermoelectric cooler plate or blanket.

9. The device of claim 1 further comprising a third shape altering, air impermeable material positioned between the non-shape altering, air impermeable enclosure and the air permeable, thermal transfer pad.

10. The device of claim 1 wherein the first shape altering, air impermeable material is a sealed aperture.

11. A negative pressure, thermal energy device comprising:
a non-shape altering, air impermeable enclosure having an appendage opening, a positive pressure opening, and a negative pressure opening;
a sealed aperture to receive a portion of a patient's appendage;
a first shape altering, air impermeable material positioned at the positive pressure opening and securely attached to the non-shape altering, air impermeable enclosure;
an operating container that releasably attaches to the non-shape altering, air impermeable enclosure, and positioned at the negative pressure opening,
(a) the non-shape altering, air impermeable enclosure, (b) the sealed aperture, (c) the first shape altering, air impermeable material, and (d) the operating container define a cavity;
furthermore, the operating container
  (a) has a thermal energy contacting surface that transfers thermal energy to the patient's body surface and interconnects to or is a component of a thermal energy generating device; and
  (b) has a vacuum source that generates a negative pressure in the cavity, the negative pressure in the cavity is sufficient to cause
    (i) the patient's veins in the cavity to vasodilate, and
    (ii) the first shape altering, air impermeable material to be pulled toward the patient to provide a positive pressure on the patient that ensures the patient's body part is positioned at the negative pressure opening to maximize the transfer of thermal energy from the thermal energy contacting surface to the patient's surface.

12. The device of claim 11 wherein the negative pressure modulates.

13. The device of claim 12 wherein the negative pressure modulates between −25 and −40 mmHg.

14. The device of claim 11 wherein the operating container has a leak aperture that allows ambient air to enter the cavity.

15. The device of claim 11 wherein the thermal energy contacting surface defines a portion of a conduit, the conduit interconnects to the thermal energy generating device, the thermal energy generating device is a hyper/hypo/normothermia fluid temperature control device, the hyper/hypo/normothermia fluid temperature control device controls the temperature of the fluid, and the fluid at the predetermined temperature circulates in the conduit.

16. The device of claim 11 wherein the thermal energy contacting surface and the thermal energy generating device is a thermal heating plate or blanket.

17. The device of claim 11 wherein the thermal energy contacting surface and the thermal energy generating device is a thermoelectric cooler plate or blanket.

18. The device of claim 11 further comprising an air permeable, thermal transfer pad removably attached to the negative pressure opening, and positioned between the non-shape altering, air impermeable enclosure and the operating container.

19. The device of claim 11 wherein the sealed aperture is a second shape altering, air impermeable material.

20. The device of claim 11 further comprising a third shape altering, air impermeable material positioned between the non-shape altering, air impermeable enclosure and the operating container.

* * * * *